United States Patent
Ooe et al.

(10) Patent No.: US 12,193,461 B2
(45) Date of Patent: Jan. 14, 2025

(54) METHOD FOR DEODORIZING KONJAC TUBER EXTRACT OR KONJAC TOBIKO CONTAINING GLUCOSYLCERAMIDE

(71) Applicant: DAICEL CORPORATION, Osaka (JP)

(72) Inventors: Kenichi Ooe, Tokyo (JP); Linghua Zhao, Shanghai (CN)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 17/880,086

(22) Filed: Aug. 3, 2022

(65) Prior Publication Data

US 2023/0051233 A1    Feb. 16, 2023

(30) Foreign Application Priority Data

Aug. 4, 2021 (CN) .......................... 202110892563.6

(51) Int. Cl.
*A23L 29/244* (2016.01)
*A23L 33/105* (2016.01)
*A61K 8/68* (2006.01)
*A61Q 19/00* (2006.01)

(52) U.S. Cl.
CPC ............ *A23L 29/244* (2016.08); *A23L 33/105* (2016.08); *A61K 8/68* (2013.01); *A61Q 19/007* (2013.01)

(58) Field of Classification Search
None
See application file for complete search history.

(56) References Cited

FOREIGN PATENT DOCUMENTS

JP    2002-281936 A    10/2002
JP    2017-88890 A    5/2017

*Primary Examiner* — Terry A McKelvey
*Assistant Examiner* — Catheryne Chen
(74) *Attorney, Agent, or Firm* — Birch, Stewart, Kolasch & Birch, LLP

(57) ABSTRACT

The present disclosure provides a method for deodorizing a konjac tuber extract or konjac tuber powder containing glucosylceramide.

With steam treatment including bringing steam into contact with a konjac tuber extract or konjac tuber powder containing glucosylceramide under a temperature condition of 100° C. or lower, a unique odor can be eliminated.

17 Claims, No Drawings

METHOD FOR DEODORIZING KONJAC TUBER EXTRACT OR KONJAC TOBIKO CONTAINING GLUCOSYLCERAMIDE

TECHNICAL FIELD

The present disclosure relates to a method for deodorizing a konjac tuber extract or konjac tuber powder containing glucosylceramide. The present disclosure also relates to a konjac tuber extract containing glucosylceramide, the konjac tuber extract having a reduced unique odor derived from an extraction raw material, and a method for producing the same.

BACKGROUND ART

Glucosylceramide contained in a konjac tuber is known to have effects such as moisture retention of the skin, improvement of skin roughness, making of beautiful skin, improvement of atopic dermatitis, and improvement of allergic dermatitis, and used in fields of food, cosmetics, medical products, and the like. It is known that glucosylceramide contained in the konjac tuber is obtained by subjecting konjac tuber powder such as Tobiko to extraction treatment with an organic solvent such as ethanol (see, for example, Patent Document 1).

However, when konjac tuber powder is subjected to extraction treatment with an organic solvent, odorous components such as aldehyde, carboxylic acid, and trimethylamine contained in the konjac tuber are also inevitably extracted along with glucosylceramide. Furthermore, these odorous components cannot be sufficiently removed even in purification treatment such as solvent fractionation. As a result, in the related art, a konjac tuber extract containing glucosylceramide also contains odorous components, and has a disadvantage of having a unique odor derived from the extraction raw material used in producing the konjac tuber extract, which may adversely affect a flavor when blended in food or the like. Accordingly, there is a demand for establishing a method for deodorizing a konjac tuber extract containing glucosylceramide, or a method for deodorizing konjac tuber powder used as an extraction raw material of the konjac tuber extract.

On the other hand, as a method for deodorizing edible oil such as salad oil, steam treatment in which the oil is brought into contact with steam is known (for example, Patent Document 2, Non-Patent Document 1, etc.). However, in the steam treatment used as the method for deodorizing edible oil, it is essential to perform the steam treatment under high temperature conditions of 200° C. or higher for deodorizing. Glucosylceramide is thermally decomposed under high temperature conditions of 200° C. or higher, and thus it is believed that the steam treatment used as the method for deodorizing edible oil is not applicable to deodorizing of the konjac tuber extract or konjac tuber powder containing glucosylceramide.

CITATION LIST

Patent Document

Patent Document 1: JP 2002-281936 A
Patent Document 2: JP 2017-88890 A

Non-Patent Literature

Non-Patent Document 1: Shunichi YOSHINO, Deodorizing Systems for Oils and Fats, Journal of Japan Oil Chemists' Society, Vol. 16, No. 5, 1967, pp. 249-258

SUMMARY OF INVENTION

Technical Problem

The present disclosure provides a method for deodorizing a konjac tuber extract or konjac tuber powder containing glucosylceramide. The present disclosure also provides a konjac tuber extract containing glucosylceramide, the konjac tuber extract having a reduced unique odor derived from an extraction raw material, and a method for producing the same.

Solution to Problem

The present inventor has made a diligent study to solve the above-mentioned problems, and found that it is possible to eliminate a unique odor derived from an extraction raw material used for producing the konjac tuber extract by performing steam treatment in which steam is brought into contact with a konjac tuber extract containing glucosylceramide under a temperature condition of 100° C. or lower. Furthermore, the present inventor has found that it is possible to eliminate the unique odor by performing the steam treatment in which steam is brought into contact with konjac tuber powder under a temperature condition of 100° C. or lower. The present disclosure has been achieved through further examinations based on these findings.

As an embodiment of the present disclosure, the following deodorizing method is exemplified.

Item 1-1. A method for deodorizing a konjac tuber extract or konjac tuber powder containing glucosylceramide, the method including
    performing steam treatment including bringing steam into contact with a konjac tuber extract or konjac tuber powder containing glucosylceramide under a temperature condition of 100° C. or lower.

Item 1-2. The deodorizing method according to item 1-1, wherein the steam treatment is performed under a condition of a vacuum degree of 0.01 to 120 kPa.

Item 1-3. The deodorizing method according to item 1-1 or 1-2, wherein in the steam treatment, 1 to 500 g of steam is brought into contact with 1 g of the konjac tuber extract or konjac tuber powder.

Item 1-4. The deodorizing method according to item 1-1 or 1-2, wherein the konjac tuber extract is an extract yielded by subjecting Tobiko of a konjac tuber to extraction treatment with an organic solvent.

Item 1-5. The deodorizing method according to item 1-1 or 1-2, wherein the konjac tuber powder is the Tobiko of the konjac tuber.

Further, as another embodiment of the present disclosure, a method for producing a konjac tuber extract and a konjac tuber extract, which will be described below, are exemplified.

Item 2-1. A method for producing a konjac tuber extract containing glucosylceramide, the method including:
    (1) subjecting a konjac tuber to extraction treatment with an organic solvent to yield a konjac tuber extract containing glucosylceramide; and (2) performing steam treatment in which steam is brought into contact with the konjac tuber extract yielded in the step (1) under a temperature condition of 100° C. or lower.

Item 2-2. The production method according to item 2-1, wherein the konjac tuber used in the step (1) is Tobiko of the konjac tuber.

Item 2-3. The production method according to item 2-1 or 2-2, wherein the steam treatment in the step (2) is performed under a condition of a vacuum degree of 0.01 to 120 kPa.

Item 2-4. The production method according to item 2-1 or 2-2, wherein in the steam treatment in the step (2), 1 to 500 g of steam is brought into contact with 1 g of the konjac tuber extract.

Item 2-5. A konjac tuber extract produced by the production method described in any one of items 2-1 to 2-4.

Furthermore, as yet another embodiment of the present disclosure, a method for producing a konjac tuber extract described below is exemplified.

Item 3-1. A method for producing a konjac tuber extract containing glucosylceramide, the method including:
(I) performing steam treatment in which steam is brought into contact with konjac tuber powder under a temperature condition of 100° C. or lower; and
(II) subjecting the konjac tuber powder yielded in the step (I) to extraction treatment with an organic solvent to yield a konjac tuber extract containing glucosylceramide.

Item 3-2. The production method according to item 3-1, wherein the konjac tuber powder used in the step (1) is Tobiko of a konjac tuber.

Item 3-3. The production method according to item 3-1 or 3-2, wherein the steam treatment in the step (I) is performed under a condition of a vacuum degree of 0.01 to 120 kPa.

Item 3-4. The production method according to item 3-1 or 3-2, wherein in the steam treatment in the step (1), 1 to 500 g of steam is brought into contact with 1 g of the konjac tuber powder.

Item 3-5. A konjac tuber extract produced by the production method described in any one of items 3-1 to 3-4.

Advantageous Effects of Invention

According to an embodiment of the deodorizing method of the present disclosure, for a konjac tuber extract containing glucosylceramide, it is possible to eliminate a unique odor derived from an extraction raw material used in producing the konjac tuber extract while retaining glucosylceramide stably. In particular, according to a preferred embodiment of the deodorizing method of the present disclosure, in a konjac tuber extract produced by using Tobiko of a konjac tuber as an extraction raw material, it is possible to eliminate a unique odor derived from the Tobiko of the konjac tuber while retaining glucosylceramide stably.

Further, according to another embodiment of the deodorizing method of the present disclosure, for konjac tuber powder, it is possible to eliminate the unique odor while retaining glucosylceramide stably. In particular, according to a preferred embodiment of the deodorizing method of the present disclosure, for Tobiko of a konjac tuber, it is possible to eliminate the unique odor while retaining glucosylceramide stably.

Furthermore, according to the production method of the present disclosure, it is possible to produce a konjac tuber extract containing glucosylceramide, in which a unique odor derived from an extraction raw material (such as Tobiko of a konjac tuber) used in producing the konjac tuber extract is reduced.

DESCRIPTION OF EMBODIMENTS

1. Deodorizing Method

An embodiment of the present disclosure is a method for deodorizing a konjac tuber extract or konjac tuber powder containing glucosylceramide, the method including performing steam treatment including bringing steam into contact with a konjac tuber extract or konjac tuber powder containing glucosylceramide under a temperature condition of 100° C. or lower. Hereinafter, a deodorizing method that is an embodiment of the present disclosure will be described in detail.

Konjac Tuber Extract or Koniac Tuber Powder

In the deodorizing method of the present disclosure, an object to be deodorized is a konjac tuber extract or konjac tuber powder containing glucosylceramide. Hereinafter, the konjac tuber extract and the konjac tuber powder will be described.

Konjac Tuber Extract

A konjac tuber extract containing glucosylceramide can be produced by subjecting a konjac tuber to extraction treatment with an organic solvent.

The konjac tuber used as an extraction raw material may be in a raw state as is, but may be subjected to pre-treatment such as grinding, cutting, or drying. The konjac tuber used as the extraction raw material is preferably in a powder shape such as rough powder, refined powder, or Tobiko. Here, the "rough powder" refers to powder produced by cutting and drying a konjac tuber. The "refined powder" refers to powder (konjac powder) produced by stamping and pulverizing the rough powder and removing the Tobiko. The "Tobiko" refers to powder that is produced as a byproduct when producing the refined powder. Among others, the Tobiko has a high glucosylceramide content and is a raw material that is not utilized as food. Therefore, in an embodiment of the deodorizing method of the present disclosure, the Tobiko is suitable as an extraction raw material of the konjac tuber extract which is an object to be deodorized.

The organic solvent used as an extraction solvent is not particularly limited as long as glucosylceramide contained in the konjac tuber can be extracted, and examples of the organic solvent include: alcohols such as methanol, ethanol, 1-propanol, 2-propanol, 1-butanol, 2-butanol, and tert-butanol; chloroform; dichloromethane: acetone; acetonitrile; ethyl acetate; hexane; pentane; and diethyl ether. In an embodiment of the deodorizing method of the present disclosure, as the extraction solvent of the konjac tuber extract to be deodorized, from the perspective of extraction efficiency of glucosylceramide, safety, and the like, ethanol, acetone, and hexane are preferably exemplified, and ethanol is more preferably exemplified. Furthermore, the organic solvent used as the extraction solvent may include water, surfactant, or the like as needed.

An amount of the organic solvent used in the extraction treatment is not particularly limited as long as glucosylceramide contained in the konjac tuber can be extracted, but is, for example, approximately from 1 to 30 times, and preferably from 1 to 10 times, by weight relative to the konjac tuber as the extraction raw material.

A temperature in the extraction treatment only need be appropriately set in consideration of a boiling point and the like of the organic solvent used, but is, for example, approximately 20 to 70° C., preferably approximately 20 to 60° C., and more preferably approximately 20 to 50° C.

A processing time of the extraction treatment is not particularly limited as long as glucosylceramide contained in the konjac tuber can be extracted, but is, for example, from 1 to 24 hours, and preferably from 2 to 10 hours.

The solvent extraction processing may be carried out by immersing or refluxing the extraction raw material in the extraction solvent. Furthermore, after the extraction treatment is performed, a residue may be recovered, and the extraction treatment may be performed again using a fresh organic solvent for the residue.

After the extraction treatment, solids are removed by solid-liquid separation so that a konjac tuber extract containing glucosylceramide is produced. The solid-liquid separation can be performed by a known method using, for example, suction filtration, a filter press, a cylinder press, a decanter, a centrifugal separator, a filtration centrifuge, or the like.

The konjac tuber extract produced by the solid-liquid separation after the extraction treatment may be subjected to the deodorizing method of the present disclosure as is, but may be subjected removal of some or all solvent and then subjected to the deodorizing method of the present disclosure. Further, the produced konjac tuber extract may be subjected to purification treatment such as solvent fractionation to remove impurities other than glucosylceramide and then subjected to the deodorizing method of the present disclosure. The purification treatment by the solvent fractionation can be performed by mixing water of 1 to 500 times in a volume ratio with respect to the konjac tuber extract and recovering an insoluble material (the konjac tuber extract containing glucosylceramide).

Konjac Tuber Powder

The konjac tuber powder may be any of rough powder, refined powder, Tobiko, and the like of a konjac tuber, but is preferably Tobiko.

Steam Treatment

In the deodorizing method of the present disclosure, steam treatment in which steam is brought into contact with the konjac tuber extract or konjac tuber powder under a temperature condition of 100° C. or lower is performed to deodorize the konjac tuber extract or konjac tuber powder.

Specifically, the steam treatment in which steam is brought into contact with the konjac tuber extract or konjac tuber powder can be performed by a steam distillation method. The steam treatment may be performed in any manner such as a batch type, a semi-continuous type, a continuous type, or the like.

A temperature condition when steam is brought into contact with the konjac tuber extract or konjac tuber powder is 100° C. or lower. In the related art, in a case where the steam treatment is performed for deodorizing purposes, a temperature condition of 200° C. or higher is employed, and it is believed that a desired deodorizing effect cannot be obtained at the low temperature condition of 100° C. or lower. In contrast, in the deodorizing method of the present disclosure, the steam treatment is performed under the low temperature condition of 100° C. or lower. With this method, it is possible to deodorize the konjac tuber extract or konjac tuber powder containing glucosylceramide effectively while retaining glucosylceramide stably. When the konjac tuber extract or konjac tuber powder is subjected to the steam treatment under a temperature condition of higher than 100° C., glucosylceramide decomposition and odor generation by thermal chemical reaction are observed, and it is impossible to reduce the odor while retaining glucosylceramide stably. In an embodiment of the deodorizing method of the present disclosure, from the perspective of achieving even more efficient reduction in odor while retaining glucosylceramide stably, the temperature condition of the steam treatment is preferably from 20 to 100° C., more preferably from 40 to 100° C., and more preferably from 60 to 100° C. In particular, in a case of deodorizing the konjac tuber extract, the steam treatment temperature condition of 40° C. or higher, particularly 60° C. or higher, facilitates prevention of solidification of the konjac tuber extract, allowing the konjac tuber extract to exhibit fluidity suitable for the steam treatment. Thus, the steam treatment can be efficiently performed.

A vacuum degree during the steam treatment is not particularly limited, but is, for example, from 0.01 to 120 kPa, preferably from 0.4 to 101.33 kPa. Here, the vacuum degree during the steam treatment refers to a pressure of gas within an apparatus for performing the steam treatment.

An amount of steam to be brought into contact during the steam treatment is, for example, from 1 to 500 g, preferably from 5 to 100 g, and more preferably from 5 to 50 g per 1 g of the konjac tuber extract or konjac tuber powder. Here, the amount of steam to be brought into contact during the steam treatment refers to a total amount of steam to be brought into contact with the konjac tuber extract or konjac tuber powder during a period from start to end of the steam treatment, and corresponds to an "blown amount of steam" in Examples described below.

A treatment time in the steam treatment may be appropriately set in accordance with an amount of the konjac tuber extract or konjac tuber powder to be treated, an amount of steam to be brought into contact, and the like, but is, for example, from 1 to 240 minutes, preferably from 10 to 180 minutes, and more preferably from 30 to 120 minutes.

The steam treatment in this manner can yield the konjac tuber extract whose unique odor derived from the extraction raw material used in producing the konjac tuber extract is eliminated, or the konjac tuber powder whose unique odor is eliminated.

The konjac tuber extract subjected to the deodorizing method of the present disclosure can be blended to be used in food, cosmetics, medical products, and the like as a source of glucosylceramide.

Further, the konjac tuber powder subjected to the deodorizing method of the present disclosure can be used as an extraction raw material to yield the konjac tuber extract containing glucosylceramide. When the extraction treatment is performed using the konjac tuber powder subjected to the deodorizing method of the present disclosure as the extraction raw material, the konjac tuber extract whose unique odor derived from the konjac tuber powder is eliminated can be produced.

2. Koniac Tuber Extract and Method for Producine Same (1)

Another embodiment of the present disclosure is a method for producing a konjac tuber extract containing glucosylceramide, the method including the following steps (1) and (2).

(1): subjecting a konjac tuber extract to extraction treatment with an organic solvent to yield a konjac tuber extract containing glucosylceramide (2): performing steam treatment including bringing steam into contact with the konjac tuber extract yielded in the step (1) under a temperature condition of 100° C. or lower is performed.

In the step (1), the konjac tuber used as the extraction raw material, the organic solvent used as the extraction solvent, the conditions of the extraction treatment, and the like are as described in the column of "Konjac tuber Extract" of "1. Deodorizing Method" described above.

In addition, the konjac tuber extract yielded by the extraction treatment in the step (1) may be subjected to the step (2) as is, but may be subjected to the step (2) after a part or all of the solvent is removed. Furthermore, the konjac tuber extract yielded by the extraction treatment may be subjected to the deodorizing method of the present disclosure after being subjected to purification treatment such as solvent fractionation to remove impurities other than glucosylceramide. The conditions for the purification treatment by solvent fractionation are as described in "Steam Treatment" of "1. Deodorizing Method" described above.

The conditions of the steam treatment in the step (2) are as described in "Steam Treatment" of "1. Deodorization Method" described above.

The konjac tuber extract produced by the production method of the present disclosure can be used as a source of glucosylceramide in, for example, food, cosmetics, medical products, and the like because its unique odor derived from the extraction raw material used in producing the konjac tuber extract is eliminated.

3. Koniac Tuber Extract and Method for Producing Same (2)

Still another embodiment of the present disclosure is a method for producing a konjac tuber extract containing glucosylceramide, the method including the following steps (I) and (II).

(I): subjecting konjac tuber powder to steam treatment including bringing steam into contact under a temperature condition of 100° C. or lower.

(II): subjecting the konjac tuber powder yielded in the step (I) to extraction treatment with an organic solvent to yield a konjac tuber extract containing glucosylceramide.

In the step (I), the type of the konjac tuber powder used and the conditions of the steam treatment are as described in "Konjac tuber Powder" and "Steam Treatment" of "1. Deodorization Method" described above.

In the step (II), the organic solvent used as the extraction solvent, the conditions of the extraction treatment, and the like are as described in "Konjac tuber Extract" of "1. Deodorizing Method" described above.

Further, the konjac tuber extract yielded by the extraction treatment of the step (II) may be used as a source of glucosylceramide as is, but may be used as a source of glucosylceramide after some or all solvent is removed as needed. Furthermore, the konjac tuber extract yielded by the extraction treatment of the step (II) may be subjected to purification treatment such as solvent fractionation to remove impurities other than glucosylceramide and then subjected to the deodorizing method of the present disclosure. The conditions for the purification treatment by solvent fractionation are as described in "Steam Treatment" of "1. Deodorizing Method" described above.

In the konjac tuber extract yielded by the production method of the present disclosure, its unique odor derived from the extraction raw material used in producing the konjac tuber extract is eliminated. Therefore, the konjac tuber extract can be used as a source of glucosylceramide in, for example, food, cosmetics, medical products, and the like.

EXAMPLES

The present disclosure is not limited in any way to the embodiments described above and the description of Examples. Various modified aspects are also included in the present invention as long as they could be readily conceived by a person skilled in the art without departing from the scope of the claims. The contents of the documents and the like shown in the present specification are cited by incorporating all the contents thereof.

Production Example: Preparation of Koniac Tuber Extract (Material that is to be Deodorized)

Extraction treatment was performed by adding 1 kg of Tobiko of a konjac tuber to 2 L of ethanol and stirring for 2 hours at room temperature. An extracted liquid was collected by solid-liquid separation after the extraction treatment. Water was added to the obtained extracted liquid in an amount of twice the amount of the obtained extracted liquid and the mixture was stirred. And then an insoluble matter was collected to yield a konjac tuber extract. When the obtained konjac tuber extract was analyzed by high performance liquid chromatography (HPLC), the glucosylceramide content was 8.2 wt. %. The konjac tuber extract obtained in this manner was used in Test Examples 1 to 3 described below.

Test Example 1: Deodorizing Test of Konjac Tuber Extract (Examination of Temperature During Steam Treatment)

Steam treatment was performed by placing 2 g of the konjac tuber extract in a flask, and blowing steam into the konjac tuber extract in the flask for 90 minutes in a state where the flask was immersed in an oil bath and heated to each temperature shown in Table 1 while a vacuum degree of 0.4 kPa was maintained in the flask. The blown amount of steam in each temperature condition (total blown amount of steam for 90 minutes) is as shown in Table 1.

The glucosylceramide content contained in the konjac tuber extract after the steam treatment was analyzed by HPLC, and the proportion of the glucosylceramide content after the steam treatment with respect to the glucosylceramide content before the steam treatment was calculated and reported as the residual ratio (%) of glucosylceramide. In addition, an odor of the konjac tuber extract after the steam treatment was evaluated in accordance with the following judgment criteria by a panelist trained with respect to scent evaluation. For comparison, a konjac tuber extract not subjected to the steam treatment was also evaluated in the same manner.

Judgment Criteria of Odor
  A: Substantially odorless.
  B: Although the panelist perceived the slight unique odor derived from the Tobiko of the konjac tuber, the panelist reported reduction of the odor as compared with that before the steam treatment, and perceived no other odor.

C1: The panelist reported no reduction of the odor as compared with that before the steam treatment, and also perceived an odor unique to the konjac tuber.

C2: The panelist reported reduction of the unique odor derived from the Tobiko of the konjac tuber, but perceived another odor.

The results are shown in Table 1. In the konjac tuber extract subjected to the steam treatment under a temperature condition of 150° C. or 130° C., the unique odor itself derived from the Tobiko of the konjac tuber was reduced, but another odor was generated along with the reduction in glucosylceramide content (Comparative Examples 2 and 3). In contrast, in the konjac tuber extract subjected to the steam treatment under a temperature condition of 60 to 150° C., the unique odor derived from the Tobiko of the konjac tuber was sufficiently eliminated, and in addition, the glucosylceramide content was also stably maintained (Examples 1 to 4). In particular, the konjac tuber extract subjected to the steam treatment under a temperature condition of 80 to 100° C. became substantially odorless, so that an excellent deodorizing effect was observed.

Note that in a case where the steam treatment was performed under a temperature condition of 80° C. or higher, the konjac tuber extract was not solidified, and sufficient fluidity was observed, which did not lead to insufficient steam treatment or difficulty in operation of steam treatment.

TABLE 1

| | | Comparative Examples | | | Examples | | | |
|---|---|---|---|---|---|---|---|---|
| | | 1 | 2 | 3 | 1 | 2 | 3 | 4 |
| Steam treatment condition | Temperature (° C.) | No steam treatment | 150 | 130 | 100 | 90 | 80 | 60 |
| | Blown amount of steam (g) | | 40.27 | 23.59 | 85.45 | 83.21 | 83.64 | 82.05 |
| Glucosylceramide residual ratio (%) | | 100.0 | 40.6 | 73.0 | 97.1 | 100.0 | 100.0 | 100.0 |
| Evaluation result of odor | | C1 | C2 | C2 | A | A | A | B |

Test Example 2: Deodorizing Test of Koniac Tuber Extract (Examination of Pressure During Steam Treatment)

Two g of a konjac tuber extract was put in a flask, and in a state where the flask was immersed in an oil bath and heated to 80° C. while the interior of the flask was maintained at each vacuum degree shown in Table 2, steam was blown into the konjac tuber extract in the flask for 60 minutes, thereby performing the steam treatment. The blown amount of steam at each vacuum degree (total blown amount of steam for 60 minutes) is as shown in Table 2.

The odor evaluation was performed in the same manner as in Test Example 1 described above for the konjac tuber extract after the steam treatment. For comparison, a konjac tuber extract not subjected to the steam treatment was also evaluated in the same manner.

The results are shown in Table 2. As a result, an excellent deodorizing effect was observed in any case of from 0.4 to 101.33 kPa of the vacuum degree during the steam treatment for the konjac tuber extract (Examples 5 to 9).

TABLE 2

| | | Comparative Examples | Examples | | | | |
|---|---|---|---|---|---|---|---|
| | | 1 | 5 | 6 | 7 | 8 | 9 |
| Steam treatment condition | Vacuum degree (kPa) | No steam treatment | 101.33 | 40 | 20 | 5 | 0.4 |
| | Blown amount of steam (g) | | 58.10 | 59.02 | 72.19 | 141.46 | 151.47 |
| Evaluation results of odor | | C1 | A | A | A | A | A |

Test Example 3: Deodorizing Test of Koniac Tuber Extract (Examination of Blown Amount of Steam During Steam Treatment)

Two g of a konjac tuber extract was put in a flask, and in a state where the flask was immersed in an oil bath and heated to 60° C. while the vacuum degree in the flask was maintained at 0.4 kPa, steam was blown into the konjac tuber extract in the flask for 60 minutes with a blown amount of steam shown in Table 3 (total amount of steam blown), thereby performing the steam treatment.

The odor evaluation was performed in the same manner as in Test Example 1 described above for the konjac tuber extract after the steam treatment. For comparison, a konjac tuber extract not subjected to the steam treatment was also evaluated in the same manner.

The results are shown in Table 3. As a result, an excellent deodorizing effect was observed in any case of 2 to 41 g of the blown amount of steam per 1 g of the konjac tuber extract (Examples 10 to 14). In particular, in a case where the blown amount of steam per 1 g of the konjac tuber extract was from 5 to 41 g, a remarkably excellent deodorizing effect was observed (Examples 10 to 13).

TABLE 3

| | | Comparative Examples | Examples | | | | |
|---|---|---|---|---|---|---|---|
| | | 1 | 10 | 11 | 12 | 13 | 14 |
| Steam treatment condition | Blown amount of steam (g) | No steam treatment | 82.05 | 65.74 | 16.19 | 9.93 | 3.9 |
| | Weight ratio of blown amount of steam (g) per 1 g of konjac tuber extract | | 41 | 33 | 8 | 5 | 2 |
| Evaluation results of odor | | C1 | A | A | A | A | B |

Test Example 4: Deodorizing Test of Tobiko of Koniac Tuber

Two g of Tobiko of a konjac tuber was put in a flask, and steam was blown into the Tobiko of the konjac tuber in the flask so as to achieve the temperature, treatment time, and blown amount of steam (total amount of steam blown) shown in Table 3 in a state where the flask was immersed in an oil bath and heated to 60° C. while the vacuum degree in the flask was maintained at 5 kPa, thereby performing the steam treatment.

Using the Tobiko after the steam treatment, extraction treatment was performed under the same conditions as those of the production example to obtain a konjac tuber extract. The odor evaluation was performed in the same manner as in Test Example 1 described above for the konjac tuber extract. In addition, for comparison, using Tobiko of a konjac tuber not subjected to the steam treatment, a konjac tuber extract was obtained under the same conditions, and the odor evaluation was performed in a similar manner.

The results are shown in Table 4. As a result, it was confirmed that performing the steam treatment at 100° C. or lower for the Tobiko of the konjac tuber was able to sufficiently eliminate the unique odor derived from the Tobiko of the konjac tuber (Examples 15 to 18). In particular, with the Tobiko of the konjac tuber subjected to the steam treatment under a temperature condition of 60 to 100° C., an almost odorless extract was obtained, and an excellent deodorizing effect was observed.

TABLE 4

| | | Comparative Examples | Examples | | | |
|---|---|---|---|---|---|---|
| | | 2 | 15 | 16 | 17 | 18 |
| Steam treatment condition | Temperature (° C.) | No steam treatment | 100 | 60 | 40 | 20 |
| | Steam treatment time (min) | | 180 | 30 | 30 | 30 |
| | Blown amount of steam (g) | | 116.65 | 80.76 | 31.4 | 7.53 |
| Evaluation results of odor | | C1 | A | A | B | B |

The invention claimed is:

1. A method for deodorizing a konjac tuber extract or konjac tuber powder containing glucosylceramide, the method comprising
performing steam treatment including bringing steam into contact with a konjac tuber extract or konjac tuber powder containing glucosylceramide under a temperature condition of 100° C. or lower.

2. The deodorizing method according to claim 1, wherein the steam treatment is performed under a condition of a vacuum degree of 0.01 to 120 kPa.

3. The deodorizing method according to claim 1, wherein in the steam treatment, 1 to 500 g of steam is brought into contact with 1 g of a konjac tuber extract or konjac tuber powder.

4. The deodorizing method according to claim 1, wherein the konjac tuber extract is an extract yielded by subjecting Tobiko of a konjac tuber, which is produced as a byproduct when producing konjac powder, to extraction treatment with an organic solvent.

5. The deodorizing method according to claim 1, wherein the konjac tuber powder is Tobiko of the konjac tuber, which is produced as a byproduct when producing konjac powder.

6. A method for producing a konjac tuber extract containing glucosylceramide, the method comprising:
(1) subjecting a konjac tuber to extraction treatment with an organic solvent to yield a konjac tuber extract containing glucosylceramide; and
(2) performing steam treatment including bringing steam into contact with the konjac tuber extract yielded in the step (1) under a temperature condition of 100° C. or lower.

7. The production method according to claim 6, wherein the konjac tuber used in the step (1) is Tobiko of a konjac tuber, which is produced as a byproduct when producing konjac powder.

8. The production method according to claim 6, wherein the steam treatment in the step (2) is performed under a condition of a vacuum degree of 0.01 to 120 kPa.

9. The production method according to claim 6, wherein in the steam treatment in the step (2), 1 to 500 g of steam is brought into contact with 1 g of the konjac tuber extract.

10. A method for producing a konjac tuber extract containing glucosylceramide, the method comprising:
(I) performing steam treatment including bringing steam into contact with konjac tuber powder under a temperature condition of 100° C. or lower; and
(II) subjecting the konjac tuber powder yielded in the step (I) to extraction treatment with an organic solvent to yield a konjac tuber extract containing glucosylceramide.

11. The production method according to claim 10, wherein the konjac tuber powder used in the step (I) is Tobiko of a konjac tuber, which is produced as a byproduct when producing konjac powder.

12. The production method according to claim 10, wherein the steam treatment in the step (I) is performed under a condition of a vacuum degree of 0.01 to 120 kPa.

13. The production method according to claim 10, wherein in the steam treatment in the step (I), 1 to 500 g of steam is brought into contact with 1 g of the konjac tuber powder.

14. A konjac tuber extract produced by the production method described in claim 6.

15. The deodorizing method according to claim 1, wherein the steam treatment is performed under a condition of a vacuum degree of 5 to 101.3 kPa.

16. The production method according to claim 6, wherein the steam treatment in the step (2) is performed under a condition of a vacuum degree of 5 to 101.3 kPa.

17. The production method according to claim 10, wherein the steam treatment in the step (I) is performed under a condition of a vacuum degree of 5 to 101.3 kPa.

* * * * *